United States Patent [19]
Ackley et al.

[11] Patent Number: 5,629,533
[45] Date of Patent: May 13, 1997

[54] OPTICAL SENSOR AND METHOD

[75] Inventors: Donald E. Ackley, Lambertville, N.J.; Thomas B. Harvey, III, Scottsdale, Ariz.

[73] Assignee: Motorola, Schaumburg, Ill.

[21] Appl. No.: 384,095

[22] Filed: Feb. 6, 1995

[51] Int. Cl.⁶ .............................. H01L 27/15; H01L 33/00
[52] U.S. Cl. ........................ 257/80; 257/103; 257/81
[58] Field of Search ............................ 257/80, 103, 88, 257/443, 10, 40, 431, 432, 93, 81; 250/227.23; 356/41; 204/418; 436/68

[56] References Cited

U.S. PATENT DOCUMENTS

| | | | |
|---|---|---|---|
| 4,892,640 | 1/1990 | Wolfbeis et al. | 204/418 |
| 5,015,843 | 5/1991 | Seitz et al. | 250/227.21 |
| 5,408,109 | 4/1995 | Heeger et al. | 250/40 |
| 5,504,323 | 4/1996 | Heeger et al. | 250/214.1 |
| 5,523,555 | 6/1996 | Friend et al. | 250/214 R |

FOREIGN PATENT DOCUMENTS 6-97487   4/1994   Japan.

OTHER PUBLICATIONS

Zhang et al., "Photonic Devices made with Semiconducting Conjugated Polymers: New Developments", Synthetic Metals, vol. 71, No. 1–3, Apr. 1995, pp. 2241–2242.

G. Yu et al., "Optocoupler Made from Semiconducting Polymers", Journal of Electronic Materials, vol. 23, No. 9, 1994, pp. 925–928.

G. Yu et al., "Dual-function semiconducting polymer devices: Light-emitting and photodetecting diodes", Appl. Phys. Lett. 64 (12), Mar. 21, 1994, pp. 1540–1542.

*Primary Examiner*—Mahshid D. Saadat
*Assistant Examiner*—Jhihan B. Clark
*Attorney, Agent, or Firm*—Eugene A. Parsons

[57] ABSTRACT

An optical sensor (10,30) uses a polymer light emitting diode (12, 31, 41, 51) to emit light detected by a polymer photodetector (13, 36, 46, 56). The polymer light emitting diode (12, 31, 41, 51) containing an indicator that reacts with an analyte and alters the light emitted by the polymer light emitting diode (12, 31, 41, 51). The change is detected by the polymer photodector (13, 36, 46, 56) and is used to detect the presence of the analyte.

10 Claims, 1 Drawing Sheet

OPTICAL SENSOR AND METHOD

BACKGROUND OF THE INVENTION

The present invention relates, in general, to sensors, and more particularly, to a novel optical sensor.

Optical sensors previously have used glass fiber optic cables as sensors to detect pH and to detect the presence of chemicals such as carbon dioxide, carbon monoxide, and ammonia. The prior optical sensors generally expose a small section of a fiber optic cable, and apply a sol-gel derived silica glass containing a chemically sensitive dye to the outside of the exposed fiber cable. When exposed to different levels of a chemical analyte, the transmissive capability of the fiber optic cable is altered thereby changing the light that passes through the cable.

One problem with the prior sensors is the manufacturing cost. A portion of the cladding must be removed in a central portion of the cable, and then the sol-gel is applied to the exposed cable. Removing the cladding and applying the sol-gel is a labor-intensive and expensive operation. Furthermore, it is difficult to produce an array of multiple sensors suitable for sensing multiple chemicals and elements. Additionally, it is difficult to control the thickness and uniformity of the sol-gel coating, thus, it is difficult to control the response time of the sensor.

Accordingly, it is desirable to have an optical sensor that is easy to manufacture, that has a low manufacturing cost, that has a well controlled response time, and that can easily be formed into an array of multiple sensor elements.

BRIEF DESCRIPTION OF THE DRAWINGS

The FIG. 1 illustrates a perspective cut-away view of a sensor in accordance with the present invention.

DETAILED DESCRIPTION OF THE DRAWINGS

Figure 1:
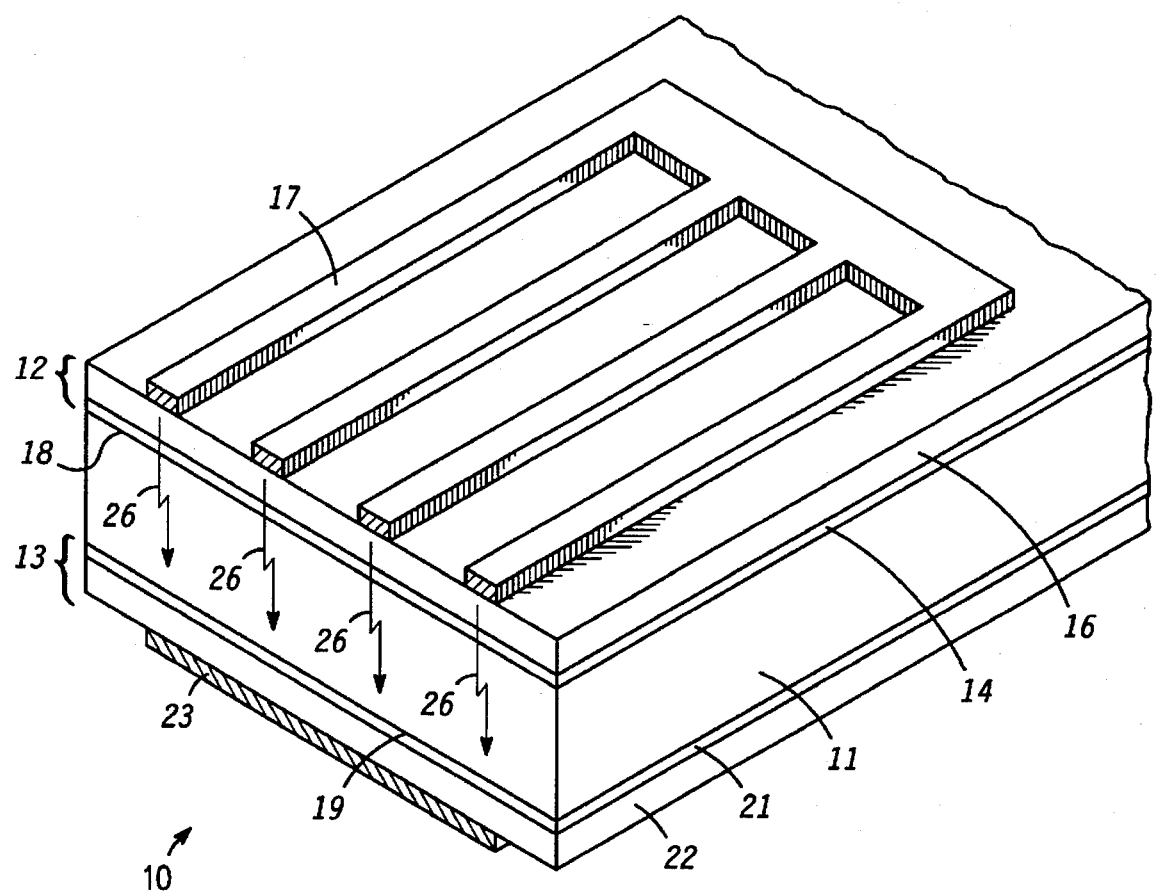

The FIG. 1 illustrates an enlarged perspective cut-away view of an optical sensor 10. Sensor 10 includes a first polymer light-emitting diode 12 on a first surface 18 of an optical substrate 11, and a polymer photodetector or detector 13 on a second surface 19 of substrate 11. Polymer light-emitting diodes and photodetectors are well known in the art. An example of a polymer light-emitting diode and photodetector can be found in a paper by G. Yu et al, "Dual-Functioning Semiconducting Polymer Devices: Light Emitting and Photodetecting Diodes", Applied Physics Letters, Vol. 64, pp. 1540–1542, 1994.

Diode 12 emits a light 26, indicated by an arrow, that passes through substrate 11. The material used for substrate 11 is optically transparent at the wavelength of light 26. Examples of such optically transparent materials include glass and optically transparent polymers such as poly (ethylene terephthalate), polycarbonates, and polystyrene. Detector 13 is positioned on surface 19 to receive and detect light 26.

As will be seen hereinafter, a first surface or conductor layer 17 of diode 12 is patterned to expose an underlying polymer 16 to an environment. Polymer 16 has an indicator that reacts with the environment and transforms light 26 exiting diode 12. Diode 12 also has a contact 14 on substrate 11 in order to provide electrical contact to diode 12. Since light passes through contact 14, a transparent material such as indium tin oxide generally is used for contact 14, although other materials may be used.

Contact 14 is formed on surface 18, and polymer 16 is formed on contact 14. Polymer 16 may be a single polymer layer or may be a plurality of polymer layers formed as a stack of multiple layers. Polymer light emitting diodes having multiple polymer layers are well known in the art. The material used for polymer 16 forms a band gap structure with the material used for layer 17 so that in the presence of an electrical bias, electrons and holes from conductor layer 17 and contact 14 are injected into polymer 16 where they recombine radiatively and emit light 26. One combination of materials that forms such a band gap structure is poly (phenylene vinylene) (PPV) for polymer 16 and a metal layer of either magnesium and silver or a metal layer of aluminum and lithium for conductor layer 17. A conducting polymer can also be used for layer 17.

Polymer 16 also includes an indicator that reacts when exposed to a particular analyte. As used herein, the term "analyte" means a chemical or chemical condition that is to be detected. Examples of analytes include particular pH levels, oxygen, carbon monoxide, carbon dioxide, and other chemicals or substances. As used herein, the term "indicator" means a substance that reacts with an analyte to transform light emitted by a polymer light emitting diode by altering the efficiency of the diode, thus, changing the intensity of the emitted light, or by changing the wavelength of light emitted from the diode. The effect the indicator has on the light depends on the type of indicator and the interaction between the indicator and the analyte. For example, some indicators alter the recombination efficiency of the diode to change the intensity of light 26. Another type of indicator, for example fluorescent dyes, change the wavelength of light emitted from the diode. Other types of indicators may expand or swell when exposed to the analyte thereby changing the thickness of polymer 16 and reducing the intensity of light 26. One example of indicators that expand or swell is soluble semiconducting polymers such as substituted PPVs, for example poly(2,5-bis(cholestanoxy)-1,4-phenylene vinylene) abbreviated as (BCHA-PPV). Some typical indicators along with some corresponding analytes are listed in the table below:

| Indicator | Analyte |
| --- | --- |
| fluorescein | oxygen, humidity, pH |
| bromocresol green | pH |
| bromocresol purple | ammonia, pH |
| $Ru(bpy)^{2+}$ | oxygen |
| $Ru(ph_2phen)3^{2+}$ | oxygen |
| cobalt chloride | humidity |
| porphyrin derivatives | heavy metals, ammonia, pH |

Polymer 16 could have the indicator as one layer of a multi-layer stack. For example a soluble semiconducting polymer could be a layer that is covered by other polymer layers. When exposed to an environment that includes organic vapors, the indictor expands, thus, reducing the intensity of light 26.

Detector 13 typically is a second polymer light emitting diode that is operated in a reverse bias mode in order to function as a photodetector. Forming detector 13 as a second polymer light emitting diode makes it easier to manufacture sensor 10. Detector 13 typically includes a contact 21 on surface 19 of substrate 11, a polymer 22 on contact 21, and a conductor layer 23 on polymer 22. Contact 21, polymer 22, and conductor layer 23 are function similar to contact 14, polymer 16, and conductor layer 17 except that polymer 22 typically does not have an indicator. Consequently, conductor layer 23 typically is not patterned. However, polymer 22 may include an indicator to either increase the sensitivity of sensor 10 to a particular analyte or to allow sensor 10 to detect more than one analyte. In such a case, conductor layer 23 typically is patterned to permit underlying polymer 22 to react with the analyte.

In order to function effectively as a sensor, it is believed that layer 17 should expose approximately fifty per cent of polymer 16 or greater. It is believed that exposing significantly less than fifty per cent of polymer 16 results is an ineffective response time. The patterned used for layer 15 can be a finger pattern, or holes in a metal layer or other pattern, although the preferred embodiment is a finger-like pattern.

The material used for polymer 22 may be the same as the material used for polymer 16, or polymer 22 could be a different material or a different thickness or both. Also, the material used for conductor layer 17 and conductor layer 23 may be the same or may be different.

Figure 2:
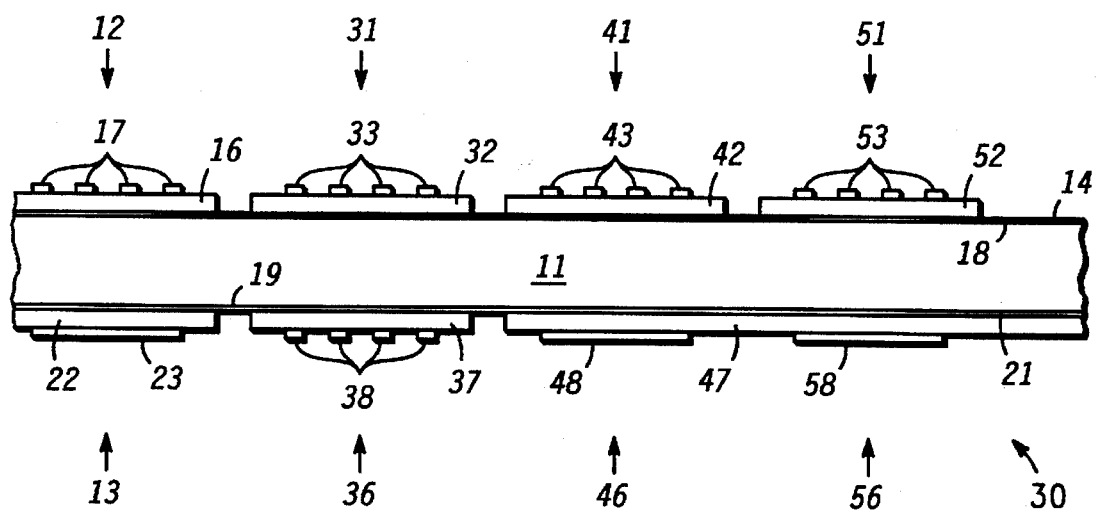
FIG. 2 illustrates a cross-sectional portion of a multi-channel sensor in accordance with the present invention.

FIG. 2 illustrates an enlarged cross-sectional view of a multi-channel optical sensor 30 that is suitable for sensing the presence of multiple analytes. Elements of FIG. 2 that have the same reference numerals as FIG. 1 are the same elements as those described in FIG. 1. Sensor 30 has a first channel that includes diode 12 and detector 13 (FIG. 1), and also has a plurality of channels near the first channel. A second channel includes a polymer light emitting diode 31 and polymer light emitting diode 36 that both have a chemical indicator. One of diodes 31 and 36 is operated in a reverse bias mode to function as a photodetector. Diode 31 has a patterned conductor layer 33 overlying a polymer 32 that has a chemical indicator. Contact 14 is common to diodes 12 and 31 and to all other diodes on first surface 18. Diode 36 has a polymer 37 containing an indicator and an overlying patterned conductor layer 38.

A third channel of sensor 30 includes a polymer light emitting diode 41 and polymer photodetector or detector 46 while a fourth channel includes a polymer light emitting diode 51 and a polymer photodetector or detector 56. Diodes 41 and 51 function similarly to diode 12, and detectors 46 and 56 function similarly to detector 13. Diode 41 has a polymer 42 containing a chemical indicator and an overlying patterned conductor layer 43. Diode 51 has a polymer 52 that contains a chemical indicator and an overlying patterned conductor layer 53. As indicated hereinbefore, a common contact 14 is used for detector 13 and diodes 12, 41, and 51.

Detectors 46 and 56 do not contain chemical indicators, thus, a layer of polymer 47 is common to both detectors 46 and 56. Detectors 46 and 56 have a conductor layer 48 and 58, respectively, on polymer 47 that each are similar to conductor layer 23.

Diodes 12, 31, 41, 51, and 36 can all have different indicators thereby allowing sensor 30 to detect the presence of multiple analytes. Alternately, the chemical indicators could be omitted from a diode in one channel allowing that channel to serve as a reference channel for sensor 30. For example, the chemical indicator could be omitted from diode 51 so that channel four can serve as a reference channel for establishing the sensitivity of sensor 30. In such a case, sensor 30 could be suitable for indicating both the presence and the quantity of a particular analyte.

By now it should be appreciated that there has been provided a novel optical sensor. Semiconductor manufacturing techniques can be used for forming sensors 10 and 30, thereby reducing the manufacturing costs. The typical polymer light emitting diode is approximately 0.1 to 0.5 microns thick and 500 microns square, consequently, the sensor has a fast response time, and the thickness is well controlled facilitating repeatability between sensors. The amount of indicator in the polymer is easy to control, thus, the sensor sensitivity is also easy to control facilitating repeatability between sensors. Multiple sensor channels can be formed on a single substrate and the resulting sensor occupies a small space. The low manufacturing cost results in a low cost multi-channel sensor having an easy to control sensitivity.

We claim:

1. An optical sensor comprising:

an optical substrate having a first surface and a second surface;

a first polymer light emitting diode having a first portion and a second portion with an underlying polymer positioned therebetween, the first portion being patterned to expose a portion of the underlying polymer, the underlying polymer includes an indicator that reacts with an analyte, the second portion of the first polymer light emitting diode being positioned on the first surface of the substrate so that the first polymer light emitting diode is positioned to emit light at a wavelength through the substrate; and a first polymer photodetector positioned on the second surface of the substrate to receive the light at the wavelength emitted through the substrate from the first polymer light emitting diode.

2. The sensor of claim 1 wherein the first portion of the first polymer light emitting diode is defined by a patterned conductor layer that is on the underlying polymer.

3. The sensor of claim 1 wherein the first polymer photodetector includes a second polymer light emitting diode positioned on the second surface of the substrate the second polymer light emitting diode having a photodetector contact on the second surface of the substrate;

a photodetector polymer on the photodetector contact; and a photodetector conductor layer on the photodetector polymer.

4. The sensor of claim 1 wherein the indicator is a second polymer included within the underlying polymer, the second polymer being selected so that it expands when exposed to the analyte.

5. The sensor of claim 1 wherein the indicator is selected from a group consisting of fluorescein, bromocresol green, bromocresol purple, $Ru(bpy)^{2+}$, $Ru(ph_2phen)_3^{2+}$, cobalt chloride, a porphyrin derivative, and a soluble semiconducting polymer.

6. The sensor of claim 1 wherein the optical substrate is glass.

7. The sensor of claim 1 wherein the optical substrate is a polymer that is transparent at the wavelength.

8. The sensor of claim 1 further including a plurality of polymer light emitting diodes on the first surface of the substrate near the first polymer light emitting diode and a plurality of photodetectors on the second surface of the substrate near the first polymer photodetector.

9. The sensor of claim 1 wherein the first portion of the first polymer light emitting diode is patterned to expose approximately fifty per cent or greater of the underlying polymer.

10. The sensor of claim 2 wherein the second portion includes a transparent contact layer on the first surface of the substrate, the underlying polymer is on the transparent contact layer, and the patterned conductor layer includes a patterned metal layer.

* * * * *